United States Patent [19]

Itob

[11] Patent Number: 5,071,558

[45] Date of Patent: Dec. 10, 1991

[54] SODIUM BICARBONATE DIALYSATE

[75] Inventor: Nobuo Itob, Tokyo, Japan

[73] Assignees: Nikkiso Co., Ltd., Tokyo; Towa Pharmaceutical Co., Ltd., Kadoma, both of Japan

[21] Appl. No.: 564,159

[22] Filed: Aug. 8, 1990

[30] Foreign Application Priority Data

Aug. 11, 1989 [JP] Japan .................................. 63-206940
Mar. 27, 1990 [JP] Japan ...................................... 1-75539

[51] Int. Cl.$^5$ ............................................. B01D 61/26
[52] U.S. Cl. ..................................... 210/542; 210/647; 252/1
[58] Field of Search .............. 210/644, 646, 647, 96.2, 210/542; 252/1, 363.5

[56] References Cited

U.S. PATENT DOCUMENTS 4,756,838  7/1988  Veltman .......................... 210/647 X

FOREIGN PATENT DOCUMENTS 34916  9/1981  European Pat. Off. .

*Primary Examiner*—Frank Spear
*Attorney, Agent, or Firm*—Oblon, Spivak, McClelland, Maier & Neustadt

[57]  ABSTRACT

A sodium bicarbonate dialysate comprising an electrolyte granule A composed mainly of sodium chloride and containing no sodium bicarbonate and an electrolyte granule B containing sodium bicarbonate, wherein the granule B is granules of sodium bicarbonate primary particles having a particle size of at most 250 μm, and the particle size of the secondary particles after granulation is from 0.1 to 10 mm.

14 Claims, No Drawings

SODIUM BICARBONATE DIALYSATE

The present invention relates to a sodium bicarbonate dialysate. More particularly, it relates to a granulated sodium bicarbonate dialysate which is easily soluble when solubilized at the time of use.

A dialysate is a reagent useful for the preparation of a dialytic solution. The dialytic solution is used to remove uremic waste by means of hemodialysis or hemodiafiltration therapy employing an artificial kidney dialyzer or peritoneal dialysis in place of the function which is usually performed by the kidney and further to supplement necessary components in blood. An attention has been drawn to a sodium bicarbonate type dialytic solution wherein sodium bicarbonate is used as an alkalizing agent, as it is physiologically preferred. As such a sodium bicarbonate dialytic solution, the one having the following electrolyte ion composition is practically employed.

| | |
|---|---|
| $Na^+$ | 120–150 mEq/l |
| $K^+$ | 0.5–3.0 mEq/l |
| $Ca^{++}$ | 1.5–4.5 mEq/l |
| $Mg^{++}$ | 0–2.0 mEq/l |
| $Cl^-$ | 90–135 mEq/l |
| $CH_3COO^-$ | 5–35 mEq/l |
| $HCO_3^-$ | 20–35 mEq/l |
| Glucose | 0–250 g/l |

The sodium bicarbonate type dialytic solution is usually prepared in such a manner that water is added to about 2.5 kg or more of the necessary electrolytes other than sodium bicarbonate to obtain a concentrate A having a volume of about 10 l in view of the solubility, and an aqueous sodium bicarbonate solution is separately prepared as the alkalizing agent also having a volume of about 10 l, so that at the time of dialysis treatment, the two solutions are mixed and diluted to a total volume of 350 l for clinical use. Sodium bicarbonate may otherwise be stored or transported in the form of a powder and is dissolved immediately prior to its use.

However, in a case where the aqueous sodium bicarbonate solution and the solution of other electrolyte components are preliminarily prepared as mentioned above, even if they are made into concentrates, their volumes and weights tend to be substantial, and there will be inconvenience in their transportation or storage.

To avoid such a drawback, if the electrolyte components are stored or transported in the form of their powders, there has been a problem that among the electrolyte components, sodium bicarbonate is particularly slow in its solubilization when the electrolyte components are dissolved in water for use.

It is an object of the present invention to provide a granular sodium bicarbonate dialysate which is advantageous for storage and transportation and is capable of readily providing a sodium bicarbonate dialytic solution and which is easy for handling and quick in the solubilization.

The present invention provides a sodium bicarbonate dialysate comprising an electrolyte granule A composed mainly of sodium chloride and containing no sodium bicarbonate and an electrolyte granule B containing sodium bicarbonate, wherein the granule B is granules of sodium bicarbonate primary particles having a particle size of at most 250 μm, and the particle size of the secondary particles after granulation is from 0.1 to 10 mm.

Further, the present invention provides a dialysate wherein the granule A is in the form of granules, and the granules A and B are mixed after granulation.

It is a feature of the present invention that the sodium bicarbonate component in the sodium bicarbonate dialysate is granulated as the granule B. This granule B is required to be granules of sodium bicarbonate primary particles having a particle size of at most 250 μm. If the particle size of the sodium bicarbonate primary particles exceeds 250 μm, the solubilization rate of the granule B tends to be slow, such being undesirable. It is preferred that the particle size of the sodium bicarbonate primary particles is at most 100 μm, since the solubilization rate will thereby be high. It is more preferred that the particle size is at most 50 μm. The particle size of the secondary particles after granulation is required to be from 0.1 to 10 mm. If the particle size of the secondary particles is less than 0.1 mm, the flowability of the granule B tends to be poor. On the other hand, if the particle size of the secondary particles exceeds 10 mm, the solubilization rate of the granule B tends to be slow, and the strength of the secondary particles tends to be low, such being undesirable.

The granule B of the present invention may contain sodium bicarbonate only or may further contain other electrolytes. The electrolytes to be combined with sodium bicarbonate include sodium chloride, potassium chloride, sodium acetate and magnesium chloride. Other components such as glucose, acetic acid or urea, may optionally be incorporated, as the case requires, so long as such incorporation does not interfere with the object of the present invention.

Among the electrolytes contained in the dialysate, a calcium component is preferably incorporated to the granule A, since it is likely to react with sodium bicarbonate to form a hardly soluble solid. A calcium component is usually prepared in the form of a chloride and is stable in the form of $CaCl_2 \cdot 2H_2O$. A magnesium component may be incorporated to the granule B at the concentration to be used for the dialysate. However, it is preferred that the magnesium component is incorporated to the granule A together with the calcium component, since it is also likely to react with sodium bicarbonate to form a hardly soluble solid. The magnesium component is usually prepared as a chloride and is stable in the form of $MgCl_2 \cdot 6H_2O$.

In the present invention, it is preferred that the granule B is granules of a mixture comprising sodium bicarbonate and from 1 to 75% by weight, based on the weight of the entire granule B, of sodium chloride and/or from 0.3 to 30% by weight, based on the weight of the entire granule B, of sodium acetate, since when dissolved in water, sodium chloride or sodium acetate having a higher solubilization rate dissolves prior to sodium bicarbonate, whereby the primary particles of sodium bicarbonate is readily dispersed in water, and the solubilization of sodium bicarbonate will be facilitated. Sodium acetate to be used here, may be in the form of an anhydride or a hydrate.

The granule B of the present invention is in the form of the granules and thus has excellent flowability and is substantially free from dusting. In spite of the granulated form, the solubilization rate is only a little lower than the primary particles alone for the above-mentioned reason. When compared in terms of the solubilization time which is the time until a solution becomes transparent after a predetermined amount of a solid is added and stirred in a predetermined amount of water, the solubilization time of the granule B of the present invention is at most 2 times that of the sodium bicarbonate primary particles.

In a case where the granule B is a mixture of sodium bicarbonate and sodium chloride, the sodium chloride content is preferably from 1 to 30% by weight. If the sodium chloride content is less than the above range, the solubilization rate in water tends to be low, such being undesirable. On the other hand, if it exceeds the above range, the solubilization rate in water likewise decreases, such being undesirable. Particularly preferred is a case where the sodium chloride content is from 1 to 5% by weight.

In a case where the granule B is a mixture of sodium bicarbonate and sodium acetate, the content of sodium acetate is preferably from 0.3 to 10% by weight as calculated as anhydrous sodium acetate. If the content of sodium acetate is less than the above range, the solubilization rate in water tends to decrease, such being undesirable. On the other hand, if it exceeds the above range, the solubilization rate in water likewise tends to decrease, such being undesirable. It is particularly preferred that the content of sodium acetate is from 0.5 to 8% by weight as calculated as anhydrous sodium acetate.

When the granule B is a mixture of sodium bicarbonate, sodium chloride and sodium acetate, it is preferred that the content of sodium chloride is from 1 to 5% by weight, and the content of sodium acetate is from 0.5 to 8% by weight as calculated as anhydrous sodium acetate. If the respective contents depart from the above ranges, the solubilization rate in water tends to decrease, such being undesirable.

In the granule B of the present invention, the electrolyte to be blended with sodium bicarbonate is preferably sodium acetate alone from the viewpoint of the solubilization rate in water. However, sodium acetate is highly hygroscopic, and therefore it is necessary to take a due care for the moisture prevention for the storage of the granule B. In the granule B, the electrolyte to be combined with sodium bicarbonate is preferably sodium chloride alone from such a viewpoint that no special consideration is required for the moisture prevention.

Further, in the present invention, when the granule B is granules of a mixture of sodium bicarbonate and glucose, the solubilization rate of the granule B increases. However, a due care is required, since the granule B containing glucose is susceptible to proliferation of bacteria.

The granule A of the present invention is composed of a mixture of all the components required for the dialysate other than those incorporated in the above granule B and contains sodium chloride as the main constituent. Among the components required for the dialysate, those other than sodium bicarbonate are relatively readily soluble in water. Therefore, the form of the granule A is not particularly limited. However, from the viewpoint of efficient handling, the granule A is preferably in the form of granules.

The granule A is preferably comprising sodium chloride, potassium chloride, calcium chloride, magnesium chloride and glucose.

In the present invention, the granules of the granule B (or the granule A) preferably have an angle of repose of at most 55°, since the flowability is thereby excellent and the handling will be easy. It is more preferred that the angle of repose is at most 50°. The pore volume of the granules is preferably from 0.05 to 1.0 cc/g. If the pore volume is less than 0.05 cc/g, the solubilization rate tends to be slow, such being undesirable. If the pore volume exceeds 1.0 cc/g, the strength of the granules tends to be low, and dusting tends to take place, such being undesirable. It is more preferred that the pore volume is from 0.05 to 0.2 cc/g. The apparent specific gravity of the granules is preferably from 0.5 to 0.9 as an aerated bulk density, and from 0.6 to 1.1 as an packed bulk density. If the apparent specific gravity is less than the above range, the strength of the granules tends to be low, and dusting tends to take place, such being undesirable. If the apparent specific gravity exceeds the above range, the solubilization rate tends to be slow, such being undesirable.

When the granule A or the granule B is to be granulated, powders of the respective components are mixed together with a suitable amount of water, and the mixture is granulated by means of various types of granulating machines. It is preferred to employ the following method, since it is thereby possible to further improve the solubility, particularly the solubility of sodium bicarbonate and the handling of the granules will be easy, and the strength will be adequate so that disintegration into powder will hardly take place, and it is possible to obtain granules having a uniform composition and excellent stability.

Namely, the particle sizes of the powders of the respective electrolytes are adjusted, then water is added in such an amount that the water content would be from 0.5 to 25% by weight. Then, the mixture is slowly mixed and granulated by means of e.g. an extrusion granulator, followed by drying to obtain a granular product. The particle sizes of the powders of the electrolytes used as the starting materials are usually at most 250 μm, preferably at most 100 μm, more preferably at most 50 μm. If the particles sizes exceeds 250 μm, the mechanical strength of the granules obtained as a final product tends to be inadequate and is susceptible to disintegration into powder, and the solubilization rate tends to be slow, such being undesirable. If the water content at the time of granulation is less than 0.5% by weight, the strength of particles tends to be low, thus leading to dusting. On the other hand, if it exceeds 25% by weight, granulation tends to be difficult. The size of the granules obtained by the granulation is preferably within a range of from 0.1 to 10 mm. If the particle size of the granules is less than this range, the flowability tends to be poor, or dusting tends to take place, whereby the handling tends to be difficult. On the other hand, if it exceeds the above range, the mechanical strength of the granules tends to be poor, and it tends to take a long time for solubilization.

At the time of drying the granules, particularly the granule B, it is preferred to employ a carbon dioxide gas atmosphere for the purpose of preventing the decomposition of sodium bicarbonate. The carbon dioxide gas concentration is preferably at a level of at least 5%. The drying is conducted usually at a temperature of from 30° to 90° C. As a specific means for drying, a band dryer, a disk dryer, a through flow dryer or a rotary dryer may, for example, be employed to obtain readily soluble stable granules having high strength and uniform composition.

In the dialysate of the present invention, a pH controlling ingredient such as acetic acid may preliminarily be incorporated in granule A for the purpose of controlling the pH after solubilization. The pH controlling ingredient may be added to the dialytic solution after solubilization.

With the dialysate of the present invention, the granules A and B are respectively granulated, then mixed for storage or transportation. In such a case, the particle sizes should be controlled at the time of granulation so that separation could not easily take place after mixing. The particle sizes of the granules A and B are preferably substantially equal and the ratio of the average particle size of the smaller component to the average particle size of a larger component is preferably at least 0.9. If the moisture prevention is adequate, sodium bicarbonate will not react with calcium or magnesium during the storage.

Now, the present invention will be described in further detail with reference to Examples. However, it should be understood that the present invention is by no means restricted to such specific Examples.

EXAMPLE 1

Sodium chloride, potassium chloride, calcium chloride dihydrate, magnesium chloride hexahydrate, sodium acetate dehydrate and glucose which were respectively pulverized to an average particle size of about 50 μm, were mixed in the following proportions, and water was further added in an amount of 1.5% by weight on dry base.

| NaCl | 74.7110 wt % |
|---|---|
| KCl | 1.7943 wt % |
| $CaCl_2.2H_2O$ | 2.2839 wt % |
| $MgCl_2.6H_2O$ | 1.2408 wt % |
| $CH_3COONa$ | 7.9296 wt % |
| Glucose | 12.0404 wt % |

The above mixture was granulated by means of a twin-screw extruder to obtain 100 kg of cylindrical granules having a diameter of 0.5 mm and a length of from 1 to 10 mm. The granules were dried for 3 hours in a batch chamber dryer adjusted at a temperature of 50° C. Then, 1.5% by weight of glacial acetic acid was further added to obtain a granule A.

This granule A is granular and had a pore volume of 0.08 $cm^3/g$ as measured by a mercury porosimeter. 100 cc of water of 15° C. was put into a 100 cc beaker, and 6 g of the granule A was put in the water and stirred at 500 rpm by a magnetic stirrer, whereby the solubilization time (the time until no solid content remained) was 2 minutes and 10 seconds. The angle of repose was 40° as measured by a powder tester, manufactured by Hosokawa Micron Corp., and thus the granule A had excellent flowability. Further, the specific gravity was 0.707 as an aerated bulk density and 0.790 as a packed bulk density.

Separately, a granule B was prepared as follows.

Firstly, sodium bicarbonate and sodium chloride which were, respectively, pulverized to an average particle size of about 50 μm, were mixed in the following proportions, and then water was added in an amount of 14% by weight on dry base, followed by mixing.

| $NaHCO_3$ | 97.60 wt % |
|---|---|
| NaCl | 2.40 wt % |

The above mixture was granulated by means of a twin-screw extruder to obtain 54 kg of cylindrical granules having a diameter of 0.5 mm and a length of from 0.5 to 5 mm. Then, the granules were dried for 3 hours in a batch chamber dryer adjusted to have a carbon dioxide concentration of 55% and a temperature of 75° C., to obtain a granule B.

This granule B was granular and had a pore volume of 0.08 $cm^3/g$ as measured by a mercury porosimeter. 100 cc of water of 15° C. was put into a 100 cc beaker, and 6.1 g of the granule B was put into the water and stirred at 500 rpm by a magnetic stirrer, whereby the solubilization time (the time until the solid content no longer remained) was 3 minutes 35 seconds. The angle of repose was 42° as measured by a powder tester, manufactured by Hosokawa Micron Corp., and the granule B was found to have excellent flowability. Further, the apparent specific gravity was 0.742 as an aerated bulk density and 0.997 as a packed bulk density.

25 g of the granule A and 6.387 g of the granule B were dissolved in water of 25° C. and adjusted to 2.967 l, whereupon the concentrations of the respective components were measured. Sodium and potassium were analyzed by an atomic absorption method, calcium and magnesium were analyzed by a chelatemetric titration method, chlorine was analyzed by titration by a Mohr's method, and total acetic acid and glucose were analyzed by liquid chromatography, and hydrogen carbonate ions were analyzed by an acid-alkali titration method. The measurement was repeated three times. The results are shown in Table 1.

Then, the changes with time of the granules A and B during the storage for a long period of time were examined. Namely, the granules A and B were respectively packaged in a sealed state and let to stand at room temperature. Immediately after the production and one month, three months, 6 months, and 12 months after the production, 2654 g of the granule A and 678 g of the granule B were dissolved in water of 25° C. and adjusted to 315 l. With respect to the solutions thus obtained, the pH and the deviations of the respective ion concentrations from those immediately after the production (the respective ion concentrations immediately after the production being evaluated to be 100) were obtained. The results are shown in Table 2.

TABLE 1

| | $Na^+$ (mEq/l) | $K^+$ (mEq/l) | $Ca^{++}$ (mEq/l) | $Mg^{++}$ (mEq/l) | $Cl^-$ (mEq/l) | $CH_3COO^-$ (mEq/l) | $HCO_3^-$ (mEq/l) | Glucose (g/l) |
|---|---|---|---|---|---|---|---|---|
| Theoretical values | 140.00 | 2.00 | 2.50 | 1.00 | 112.50 | 10.22 | 25.00 | 1.00 |
| n1 | 140.36 | 2.01 | 2.52 | 1.03 | 111.92 | 10.18 | 25.02 | 0.98 |
| n2 | 140.94 | 2.01 | 2.53 | 1.04 | 111.64 | 10.24 | 25.07 | 0.97 |
| n3 | 140.13 | 2.03 | 2.52 | 1.03 | 111.64 | 10.24 | 25.07 | 0.98 |
| Average | 140.48 | 2.02 | 2.52 | 1.03 | 111.73 | 10.22 | 25.05 | 0.98 |

TABLE 2

| | Immediately after the production | 1 month later | 3 months later | 6 months later | 12 months later |
|---|---|---|---|---|---|
| $Na^+$ | 100 | 100 | 99.9 | 99.9 | 99.7 |
| $K^+$ | 100 | 100 | 99.8 | 99.7 | 99.6 |
| $Ca^{++}$ | 100 | 100 | 99.9 | 99.7 | 99.7 |
| $Mg^{++}$ | 100 | 100 | 99.9 | 99.7 | 99.8 |
| $Cl^-$ | 100 | 100 | 99.9 | 99.7 | 99.7 |
| $CH_3COO^-$ | 100 | 100 | 99.9 | 99.8 | 99.6 |
| $HCO_3^-$ | 100 | 100 | 100 | 100 | 100 |
| Glucose | 100 | 100 | 100 | 100 | 100 |
| pH | 7.22 | 7.25 | 7.23 | 7.30 | 7.28 |

From Tables 1 and 2, it is evident that the dialysate of the present invention comprising the granules A and B, can be prepared with good reproducibility and is stable with time, and even after the storage for a long period of time, a dialytic solution which is substantially not different from immediately after the production, can be reproduced. In Table 2, the contents of the respective components gradually decrease. This is believed to be due to the influence of the moisture permeated through the package material.

EXAMPLES 2 TO 9 AND COMPARATIVE EXAMPLE 1

Sodium chloride, sodium acetate and glucose which were respectively pulverized to an average particle size of 50 μm, were used, and a granule B were prepared in the same manner as in Example 1 by the blending, granulation and drying under the conditions as identified in Table 3. The properties of the granule B were measured and the results are shown in Table 3. Example 9 represents granules of sodium bicarbonate alone, and Comparative Example 1 represents sodium bicarbonate primary particles prior to granulation.

verized to an average particle size of about 50 μm, were mixed in the following proportions, and further 5% by weight of water was added, followed by mixing.

| NaCl | 80.389 wt % |
|---|---|
| KCl | 2.580 wt % |
| $CaCl_2.2H_2O$ | 3.573 wt % |
| $MgCl_2.6H_2O$ | 2.104 wt % |
| $CH_3COONa.3H_2O$ | 11.354 wt % |

The above mixture was granulated by a twin screw extruder to obtain 500 kg of granules having an average particle size of 450 μm. Then, the above granules were dried for three hours in a batch chamber dryer in an atmosphere adjusted to contain 0.5% of acetic acid gas and at a temperature of 50° C. to obtain a granule A. The granule A thus obtained was granular with an average particle size of 0.45 mm and an angle of repose of 40° and exhibited excellent flowability.

On the other hand, 5% by weight of water was added to sodium bicarbonate pulverized to have an average particle size of about 50 μm, followed by mixing. The mixture was granulated by a twin screw extruder to obtain 200 kg of granules having an average particle size of 450 μm. Then, the granules were dried for three hours in a batch chamber dryer under an atmosphere adjusted to have a carbon-dioxide gas concentration of 20% at a temperature of 50° C. to obtain a granule B. The granule B was granular with an average particle size of 0.45 mm and exhibited excellent flowability.

Then, the granules A and B were mixed in a weight ratio of 2.856:1 to obtain 500 kg of a powder mixture. The mixture of the granules A and B thus obtained (hereinafter referred to as a dialysate) had an angle of repose of 40° and exhibited excellent flowability, and the solubilization rate when resolved in water at 15° C.

TABLE 3

| | Proportions (wt %) | | Amount of water added for granulation (wt %) | Apparent specific gravities | | Angle of repose (degree) | Solubilization time (min, sec) |
|---|---|---|---|---|---|---|---|
| | Sodium bicarbonate | Blended material | | Aerated bulk* density | Packed bulk density | | |
| Example 1 | 97.60 | Sodium chloride 2.40 | 14 | 0.742 | 0.997 | 42 | 3'35" |
| Example 2 | 95.24 | Sodium chloride 4.76 | 13 | 0.752 | 1.028 | 46 | 4'10" |
| Example 3 | 99.30 | Sodium chloride 0.70 | 13 | 0.671 | 0.971 | 45 | 3'57" |
| Example 4 | 98.11 | Sodium acetate 1.89 | 8 | 0.690 | 0.995 | 44 | 2'12" |
| Example 5 | 93.68 | Sodium acetate 6.32 | 11 | 0.734 | 0.998 | 46 | 2'52" |
| Example 6 | 99.50 | Sodium acetate 0.50 | 9 | 0.753 | 1.020 | 46 | 3'58" |
| Example 7 | 96.81 | Sodium chloride 2.38 Sodium acetate 0.81 | 13 | 0.738 | 0.996 | 43 | 3'40" |
| Example 8 | 97.28 | Glucose 2.72 | 11 | 0.743 | 1.013 | 46 | 2'50" |
| Example 9 | 100 | — | 10 | 0.720 | 0.992 | 47 | 4'19" |
| Comparative Example 1 | 100 | — | — | — | — | — | 2'40" |

EXAMPLE 10

Sodium chloride, potassium chloride, calcium chloride dihydrate, magnesium chloride hexahydrate and sodium acetate trihydrate which were respectively pulwas 3 minutes. Five samples (9.7171 g) were optionally taken from the above dialysate and dissolved with water of 25° C. in a total volume of 1000 l each. The results are shown in Table 4.

TABLE 4

| | (Unit: mEq/l) | | | | | | |
|---|---|---|---|---|---|---|---|
| | $Na^+$ | $K^+$ | $Ca^{++}$ | $Mg^{++}$ | $Cl^-$ | $CH_3COO^-$ | $HCO_3^-$ |
| Theoretical values | 135 | 2.5 | 3.5 | 1.5 | 106.5 | 6 | 30 |
| n1 | 135.7 | 2.5 | 3.2 | 1.5 | 106.0 | 5.8 | 29.6 |
| n2 | 134.9 | 2.5 | 3.6 | 1.5 | 105.5 | 5.9 | 29.8 |
| n3 | 135.5 | 2.5 | 3.5 | 1.4 | 107.3 | 6.2 | 30.3 |
| n4 | 134.3 | 2.5 | 3.4 | 1.5 | 107.0 | 6.0 | 30.0 |
| n5 | 134.7 | 2.4 | 3.7 | 1.5 | 106.8 | 6.2 | 30.2 |

TABLE 4-continued

| | Na+ | K+ | Ca++ | Mg++ | Cl− | CH3COO− | HCO3− |
|---|---|---|---|---|---|---|---|
| | | | (Unit: mEq/l) | | | | |
| Average | 135.02 | 2.48 | 3.48 | 1.5 | 106.52 | 6.02 | 29.98 |

From the above Table 4, it is evident that when this dialysate was sampled randomly and dissolved, all of the five samples were reproduced as dialytic solutions having very uniform compositions. Then, the change with time of the dialysate of the present invention during the storage for a long period of time was examined. Namely, the obtained dialysate was packaged in a sealed condition and let to stand at room temperature. Immediately after the production, and upon expiration of one month, three months, 6 months and 12 months, a predetermined amount (9.7171 g) was sampled and dissolved with water of 25° C. in a total volume of 1000 ml. With respect to the solutions thus obtained, the pH and the deviation of the respective ion concentrations from those immediately after the production (the concentrations of the respective ions immediately after the production being evaluated as 100) were determined. The results are shown in Table 5.

TABLE 5

| | Immediately after the production | 1 month later | 3 months later | 6 months later | 12 months later |
|---|---|---|---|---|---|
| Na+ | 100 | 100 | 100 | 100.15 | 100.20 |
| K+ | 100 | 100 | 100 | 100.05 | 100.10 |
| Ca++ | 100 | 100 | 100 | 100.05 | 100.10 |
| Mg++ | 100 | 100 | 100 | 100.10 | 100.15 |
| Cl− | 100 | 100 | 100 | 100.17 | 100.25 |
| CH3COO− | 100 | 100 | 99.90 | 99.35 | 99.25 |
| HCO3− | 100 | 100 | 99.90 | 99.55 | 99.50 |
| pH | 7.18 | 7.20 | 7.25 | 7.35 | 7.37 |

From Table 5, it is evident that this dialysate is very stable with time and can be reproduced as a dialytic solution which does not substantially change from immediately after the production, even after the storage for a long period of time.

What is claimed is:

1. A sodium bicarbonate dialysate comprising an electrolyte composition A composed mainly of sodium chloride and containing no sodium bicarbonate and an electrolyte granule B containing sodium bicarbonate, wherein the granule B is granules of sodium bicarbonate primary particles having a particle size of at most 250 μm, and the particle size of he secondary particles after granulation is from 0.1 to 10 mm.

2. The dialysate according to claim 1, wherein the granulation of the granule B is carried out by adding water to a powder of its components so that the water content is from 0.5 to 25% by weight, followed by mixing, granulation and drying.

3. The dialysate according to claim 1 or 2, wherein the granule B is granules of a mixture comprising sodium bicarbonate and from 1 to 75% by weight, based on the weight of the entire granule B, of sodium chloride.

4. The dialysate according to claim 1 or 2, wherein the granule B is granules of a mixture comprising sodium bicarbonate and from 0.3 to 30% by weight, based on the weight of the entire granule B, of sodium acetate.

5. The dialysate according to claim 3, wherein the granule B contains from 1 to 5% by weight of sodium chloride.

6. The dialysate according to claim 1 or 2, wherein the solubilization time of the granule B is at most 2 times that of the sodium bicarbonate primary particles.

7. The dialysate according to claim 1 or 2, wherein the composition A is in the form of granules.

8. The dialysate according to claim 7, wherein the angle of repose of the granule A or the granule B is at most 55°.

9. The dialysate according to claim 7, wherein the apparent specific gravity of the granule A or the granule B is from 0.5 to 0.9 as an aerated bulk density and from 0.6 to 1.1 as a packed bulk density.

10. The dialysate according to claim 7, wherein the pore volume of the granule A or the granule B is from 0.05 to 1.0 cc/g.

11. The dialysate according to claim 7, wherein the granule A and he granule B are mixed after granulation.

12. The dialysate according to claim 1 or 2, wherein the composition A comprises sodium chloride, potassium chloride, calcium chloride, magnesium chloride and glucose.

13. The dialysate according to claim 3, wherein the drying is conducted in an atmosphere of carbon dioxide gas and/or acetic acid gas.

14. A sodium bicarbonate dialysate comprising an electrolyte granule A composed mainly of sodium chloride and containing no sodium bicarbonate and an electrolyte composition B containing sodium bicarbonate, wherein the granule A comprises sodium chloride, calcium chloride and magnesium chloride and wherein the granule A incorporates a pH controlling ingredient.

* * * * *

UNITED STATES PATENT AND TRADEMARK OFFICE
CERTIFICATE OF CORRECTION

PATENT NO. : 5,071,558

DATED : December 10, 1991

INVENTOR(S) : Nobuo Itoh

It is certified that error appears in the above-identified patent and that said Letters Patent is hereby corrected as shown below:

<u>TITLE PAGE</u>

The inventor's name is misspelled, should be, --Nobuo Itoh--.

Signed and Sealed this

Twenty-seventh Day of April, 1993

*Attest:*

MICHAEL K. KIRK

*Attesting Officer*      *Acting Commissioner of Patents and Trademarks*